US012559519B2

(12) United States Patent
Nagy et al.

(10) Patent No.: US 12,559,519 B2
(45) Date of Patent: *Feb. 24, 2026

(54) PROCESS FOR PURIFYING MONOCLOCAL ANTIBODIES

(71) Applicant: Fujifilm Diosynth Biotechnologies UK Limited, Billingham (GB)

(72) Inventors: Tibor Nagy, Billingham (GB);
Jonathan Haigh, Billingham (GB);
Charles Heise, Billingham (GB);
Andrew Topping, Billingham (GB);
James Pullen, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 1047 days.

This patent is subject to a terminal disclaimer.

(21) Appl. No.: 17/634,672

(22) PCT Filed: Aug. 6, 2020

(86) PCT No.: PCT/GB2020/051882
§ 371 (c)(1),
(2) Date: Feb. 11, 2022

(87) PCT Pub. No.: WO2021/028658
PCT Pub. Date: Feb. 18, 2021

(65) Prior Publication Data
US 2022/0275024 A1 Sep. 1, 2022

(30) Foreign Application Priority Data
Aug. 15, 2019 (GB) ..................................... 1911685

(51) Int. Cl.
| | |
|---|---|
| *C07K 1/36* | (2006.01) |
| *B01D 15/14* | (2006.01) |
| *B01D 15/18* | (2006.01) |
| *B01D 15/36* | (2006.01) |
| *B01D 15/38* | (2006.01) |
| *B01D 61/14* | (2006.01) |
| *C07K 1/18* | (2006.01) |
| *C07K 1/22* | (2006.01) |
| *C07K 1/34* | (2006.01) |
| *C07K 16/06* | (2006.01) |

(52) U.S. Cl.
CPC ................ *C07K 1/36* (2013.01); *B01D 15/14* (2013.01); *B01D 15/1871* (2013.01); *B01D 15/362* (2013.01); *B01D 15/363* (2013.01); *B01D 15/3809* (2013.01); *B01D 61/145* (2013.01); *C07K 1/18* (2013.01); *C07K 1/22* (2013.01); *C07K 1/34* (2013.01); *C07K 16/065* (2013.01); *B01D 2311/2623* (2013.01); *B01D 2311/2626* (2013.01); *B01D 2315/16* (2013.01)

(58) Field of Classification Search
None
See application file for complete search history.

(56) References Cited

U.S. PATENT DOCUMENTS

| | | | | |
|---|---|---|---|---|
| 4,861,488 | A * | 8/1989 | Kenney | .............. B01D 15/3809 |
| | | | | 73/61.53 |
| 6,365,395 | B1 | 4/2002 | Antoniou | |
| 2011/0073548 | A1 | 3/2011 | Williams et al. | |
| 2013/0260419 | A1 | 10/2013 | Ransohoff et al. | |
| 2014/0251911 | A1 | 9/2014 | Skudas | |
| 2019/0009215 | A1 | 1/2019 | Heise et al. | |
| 2022/0325231 | A1 * | 10/2022 | Nagy | ........................ C07K 1/16 |
| 2022/0333060 | A1 * | 10/2022 | Nagy | .................. B01D 61/145 |

FOREIGN PATENT DOCUMENTS

| | | | | |
|---|---|---|---|---|
| JP | 2014-534055 | A | 12/2014 | |
| WO | WO-2009058737 | A1 * | 5/2009 | .............. C07K 1/16 |
| WO | WO-2010019148 | A1 * | 2/2010 | ............. B01D 15/08 |
| WO | 2017118835 | A1 | 7/2017 | |

OTHER PUBLICATIONS

Petrides, Demetri et al. "Biopharmaceutical Process Optimization with Simulation and Scheduling Tools." Bioengineering (Basel, Switzerland) vol. 1,4 (2014): 154-187. doi:10.3390/bioengineering1040154.
Nandi, Somen et al. "Techno-economic analysis of a transient plant-based platform for monoclonal antibody production." mAbs vol. 8,8 (2016): 1456-1466. doi:10.1080/19420862.2016.1227901.
Yang, Ou et al. "Comparison between Batch and Continuous Monoclonal Antibody Production and Economic Analysis." Industrial & Engineering Chemistry Research vol. 58,15 (2019): 5851-5863. doi:10.1021/acs.iecr.8b04717.
Sep. 23, 2024 (EP) EPO Examination Report (Art 94 EPC) in respect of EP Application No. 20754810.8.

(Continued)

*Primary Examiner* — Noble E Jarrell
(74) *Attorney, Agent, or Firm* — Banner & Witcoff, Ltd.

(57) ABSTRACT

A process for purifying a liquid feedstock comprising a monoclonal antibody and impurities, the process comprising passing the liquid feedstock through an apparatus comprising at least two processing units, each such unit producing a product stream containing purified monoclonal antibody and optionally a waste stream comprising at least some of the impurities, wherein each unit comprises specified components (i) to (v) which include a multiple inlet flow-controller comprising two or more variable flow inlet valves for in situ production of a bioprocessing liquid by combining at least two liquids in a desired ratio. One of the units performs chromatography and another performs viral inactivation. The units may be essentially the same except for a device they contain, leading to advantages in terms of simplicity, cost and ease of operation, lower risk of operator error, easier maintenance and lower inventory of spare parts.

29 Claims, 2 Drawing Sheets

(56)        References Cited

OTHER PUBLICATIONS

Oct. 11, 2024 (JP) Notice of Reasons for Rejection in respect of JP Application No. 2022-508995.
Feb. 18, 2021 (WO) Written Opinion of the International Searching Authority issued in respect of International Application No. PCT/GB2020/051882.
Feb. 8, 2022 (WO) International Preliminary Report on Patentability issued in respect of International Application No. PCT/GB2020/051882.

* cited by examiner

| 1. Protein A Affinity Chromatography |
| --- |

| 2. Viral Inactivation |
| --- |

| 3. Cation Exchange Chromatography |
| --- |

| 4. Anion Exchange Chromatography |
| --- |

| 5. Removal of inactivated viruses |
| --- |

| 6. Concentration and optionally performing buffer exchange of the product stream |
| --- |

Product stream collected

PROCESS FOR PURIFYING MONOCLOCAL ANTIBODIES

RELATED APPLICATIONS

This application is a National Stage Application under 35 U.S.C. 371 of co-pending PCT application PCT/GB2020/051882 designating the United States and filed Aug. 6, 2020; which claims the benefit of GB Application number 1911685.4 and filed Aug. 15, 2019 each of which are hereby incorporated by reference in their entireties.

This invention relates to a process for purifying monoclonal antibodies.

Monoclonal antibodies ("mAbs") have attracted much attention in recent years, particularly for therapeutic applications. mAbs are commonly produced by culturing recombinant host cells which have been engineered to express the desired mAb. The mAb is then recovered from the culture medium by methods typically comprising a number of processing operations (sometimes called "unit operations").

Apparatus for purifying mAbs is known in the art and typically comprises a number of very different processing units arranged in series, wherein each unit performs an individual processing operation. The processing units usually comprise at least two pumps to move liquid through the unit. Typically the units are provided by different manufacturers who specialise in devices for performing a particular processing operation (e.g. filtration, chromatography etc.). The apparatus used for the commercial scale manufacture of mAbs is extremely bulky and requires extensive floor space and infrastructure. Additionally, whilst some commonality of processing units can be achieved for several of the processing operations, the design of units for certain unit operations, such as viral inactivation and/or ultrafiltration, differ substantially from those for, for example, chromatographic purification. This means that either more space is required to accommodate two or more sets of processing units, or that the interoperability and control of the apparatus for the stages is inordinately complex. Furthermore, operators require extensive training on each of the different types of processing unit employed because the units are so different from each other. The lack of similarity between many of the processing units currently used for mAb manufacture means that a large inventory of spare parts is required. Still further, the lack of similarity between many of the units complicates routine maintenance because engineers need to learn how to service processing units of very different construction. Apparatus requiring different bioprocessing liquids (e.g. buffers, eluents etc.) for different processing operations are also at great risk of operator error if the wrong, externally-prepared, bioprocessing liquid is provided at the wrong stage, potentially risking the failure of a highly expensive batch of mAb. Accordingly, a simplified and broadly-applicable apparatus is desirable with lower risk of operator error.

According to a first aspect of the present invention, there is provided a process for purifying a liquid feedstock comprising a monoclonal antibody (mAb) and impurities, the process comprising passing the liquid feedstock through an apparatus comprising at least two processing units, each such unit producing a product stream containing purified monoclonal antibody and optionally a waste stream comprising at least some of the impurities, wherein each unit comprises the following components (i) to (v):

(i) an inlet for the liquid feedstock;
(ii) a multiple inlet flow-controller comprising two or more variable flow inlet valves for producing a bioprocessing liquid from at least two other liquids to be combined in a desired ratio;
(iii) a means for combining the liquid feedstock and the bioprocessing liquid to produce a device feed and/or for combining the at least two other liquids to prepare the bioprocessing liquid;
(iv) a device for performing a processing operation on the liquid feedstock or on the device feed, the device comprising an inlet for the device feed and/or the liquid feedstock and an outlet for a product stream; and
(v) a means for imparting flow of the liquid feedstock, the at least two liquids, the bioprocessing liquid, the device feed, the product stream and the optional waste stream;
wherein:
(I) the liquid feedstock is fed through inlet (i) and is combined with bioprocessing liquid in the means (iii) and then fed through the device (iv) or is combined with the bioprocessing liquid in the device (iv), in either case to give the product stream and optionally a waste stream which exit the unit;
(II) the units are arranged in series such that the liquid feedstock for the second and any subsequent units comprises the product stream from the preceding unit;
(III) the device (iv) in at least one of the at least two processing units performs the processing operation of chromatography; and
(IV) the device (iv) in at least one of the at least two processing units performs the processing operation of viral inactivation.

The present invention provides a process which may be performed on a manufacturing scale and offers many advantages over prior processes, particularly in terms of simplicity, cost and ease of operation, lower risk of operator error, easier maintenance and lower inventory of spare parts.

In this specification the phrase "processing unit" is often abbreviated to "unit" and the two are used interchangeably. Component (iii) is often abbreviated to "mixer (iii)" for simplicity. Component (iv) is often referred to as "device (iv)" for simplicity.

BRIEF DESCRIPTION OF THE DRAWINGS

In the accompanying drawings:

FIG. 1 illustrates how the feedstock from a cell culture harvest may be purified by a process according to the invention. A clarified feed cell culture harvest acts as the feedstock for the first processing unit which comprises a Protein A affinity chromatography device. Then the liquid feedstock for the second and each subsequent unit comprises the product stream from the preceding unit. Each unit can also produce a waste stream (not shown), although this is not always the case. For example, a viral inactivation unit typically produces only a product stream which differs from the feedstock only in that any viruses which were present in the feedstock have been inactivated. Furthermore, a simple filtration unit may also produce only a product stream (i.e. no waste stream) when impurities are retained on the filter of that unit. Viruses inactivated in the viral inactivation unit 2. may be removed by a later unit (e.g. a viral filtration/removal unit). The order of the units in a preferred process according to the present invention are shown as steps 1. to 6. Finally the product stream containing the mAb purified by units 1. to 6. is collected.

FIG. 2 is described in more detail in the Examples section below.

Figure 1:
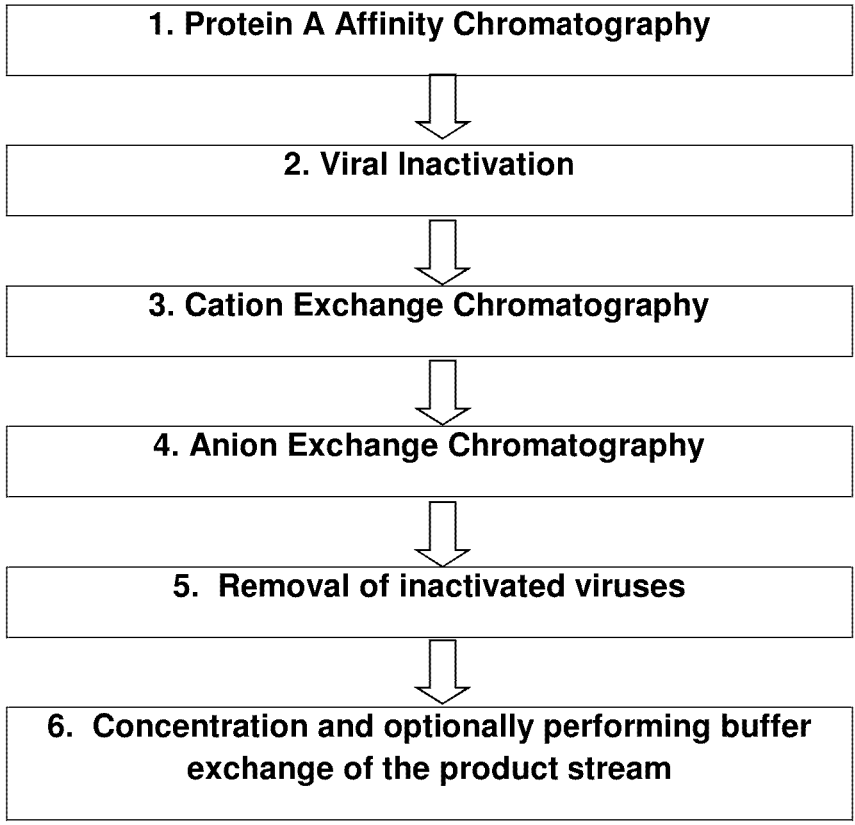
FIG. 1 is a illustrates a schematic of an embodiment of the present process.
Figure 1:

Each unit typically performs one processing operation.

The number of processing units is not particularly limited and depends to a large extent of the purification steps required to convert the liquid feedstock into a form suitable for a desired purpose, for example for formulation into a medicament. In some embodiments, the apparatus comprises two units (e.g. for performing two processing operations). In other embodiments, the apparatus comprises more than two units, for example (at least) three, four, five, six, seven, eight, nine or more units, preferably each unit having the features (i) to (v) described above. Although the process may further comprise two or more units which operate in parallel, it is preferred that all of the units used in the process are arranged in series. In many highly preferred embodiments, the process operation performed in each unit differs from the process operation used in all of the other units. Thus although the apparatus may contain, for example, more than one unit for performing chromatography, each such chromatography unit or the way it is used preferably differs from the other unit(s) for performing chromatography.

In certain embodiments, each unit comprises a flow path which is substantially the same as the flow path in at least half, more preferably all, of the other units.

Preferably each unit prepares its mixed bioprocessing liquid (in situ) during the process. In this way, the risk of an operator using the wrong, externally-prepared bioprocessing liquid intended for a different process operation is avoided.

Preferably the apparatus further comprises one or more unit for performing one or more of the following process operations, in each case the unit comprising components (i) to (v):

removing any viruses from its liquid feedstock;
   ultrafiltration of its feedstock in order to provide a concentrate comprising the desired mAb;
   diafiltration of its feedstock in order to buffer the target material at a pH at which the desired mAb is stable; and
   tangential flow filtration, including recirculating and single pass tangential flow filtration.

In a preferred embodiment the apparatus comprises processing units comprising devices for performing the following processing operations, preferably in the order stated: Protein A chromatography, viral inactivation, cation exchange chromatography, anion exchange chromatography, viral filtration (removal of inactivated viruses) and concentration of the product feed (e.g. by ultrafiltration and/or diafiltration performed in a single unit or in separate units).

The size of each unit is not particularly limited. However for industrial scale purification, each unit is preferably 1 to 2.2 meters high (more preferably 1.5 to 2 meters high), 0.5 to 1.2 meters wide (more preferably 0.75 to 1 meters wide) and 0.5 to 1 meters deep (more preferably 0.6 to 0.9 meters deep).

Preferably each unit is fitted with wheels and optionally a brake to prevent unwanted movement of the unit. This enables the units to be positioned, moved and replaced with ease.

Preferably the apparatus comprises the following units arranged in series, preferably in the order listed, each unit comprising the components (i) to (v) and with the product feed of each unit being used as the feedstock for the next unit or, if there is no next unit, the product feed being collected:

a. a unit for performing a first chromatographic purification of the mAb, preferably by affinity chromatography;

b. a unit for inactivation of any viruses which may be present in the liquid feedstock;
   c. a unit for performing a second chromatographic purification of the mAb, preferably by ion exchange chromatography;
   d. a unit for performing a third chromatographic purification of the mAb, preferably by ion exchange chromatography;
   e. a unit for removal of any inactivated viruses; and
   f. a unit for concentrating and/or performing buffer exchange of the product stream from the preceding unit.

In some embodiments, the second chromatographic purification comprises anion exchange and the third chromatographic purification comprises cation exchange. In other embodiments, the second chromatographic purification comprises cation exchange and the third chromatographic purification comprises anion exchange.

Thus in one preferred embodiment the apparatus comprises the following units arranged in series, preferably in the order listed, each unit comprising the components (i) to (v) and with the product feed of each unit being used as the feedstock for the next unit or, if there is no next unit, the product feed being collected:

a. a unit for performing chromatographic purification of the mAb by affinity chromatography;
   b. a unit for inactivation of any viruses which may be present in the liquid feedstock; and
   c. a unit for performing chromatographic purification of the mAb by ion exchange chromatography.

In another preferred embodiment the apparatus comprises the following units arranged in series, preferably in the order listed, each unit comprising the components (i) to (v) and with the product feed of each unit being used as the feedstock for the next unit or, if there is no next unit, the product feed being collected:

a. a unit for performing chromatographic purification of the mAb by affinity chromatography;
   b. a unit for inactivation of any viruses which may be present in the liquid feedstock;
   c. a unit for performing chromatographic purification of the mAb by cation exchange chromatography; and
   d. a unit for performing chromatographic purification of the mAb by anion exchange chromatography.

In another preferred embodiment the apparatus comprises the following units arranged in series, preferably in the order listed, each unit comprising the components (i) to (v) and with the product feed of each unit being used as the feedstock for the next unit or, if there is no next unit, the product feed being collected:

a. a unit for performing chromatographic purification of the mAb by affinity chromatography;
   b. a unit for inactivation of any viruses which may be present in the liquid feedstock;
   c. a unit for performing chromatographic purification of the mAb by cation exchange chromatography;
   d. a unit for performing chromatographic purification of the mAb by anion exchange chromatography; and
   e. a unit for removal of any inactivated viruses.

In another preferred embodiment the apparatus comprises the following units arranged in series, preferably in the order listed, each unit comprising the components (i) to (v) and with the product feed of each unit being used as the feedstock for the next unit or, if there is no next unit, the product feed being collected:

a. a unit for performing chromatographic purification of the mAb by affinity chromatography;

b. a unit for inactivation of any viruses which may be present in the liquid feedstock;

c. a unit for performing chromatographic purification of the mAb by cation exchange chromatography;

d. a unit for performing chromatographic purification of the mAb by anion exchange chromatography;

e. a unit for removal of any inactivated viruses: and f. a unit for concentrating and/or performing buffer exchange of the product stream from the preceding unit.

Preferably the units are arranged in series in the order listed herein, e.g. in an apparatus comprising units a. to f. preferably the units are arranged in series in the order a., b., c., d., e., then f.

Preferably at least one of the units (preferably at least half of the units, more preferably all of the units) further comprises a pressure sensor located upstream of component (iv).

Preferably at least one of the units (preferably at least half of the units, more preferably all of the units) further comprises a pressure sensor located downstream of component (iv).

Preferably at least one of the units (preferably at least half of the units, more preferably all of the units) further comprises a UV sensor located downstream of component (iv).

Preferably at least one of the units (preferably at least half of the units, more preferably all of the units) further comprises a pH sensor located downstream of component (iv).

Preferably at least one of the units (preferably at least half of the units, more preferably all of the units) further comprises a conductivity sensor located downstream of component (iv).

In a preferred embodiment at least 75% of the component parts of each unit other than component (iv) are identical to the component parts used in at least 80% of the other units of the apparatus. Preferably at least 85% of the component parts of each unit other than component (iv) are identical to the component parts used in at least 80% of the other units of the apparatus. Especially preferably at least 95% of the component parts of each unit other than component (iv) are identical to the component parts used in at least 80%, more preferably at least 90%, of the other units of the apparatus. In a particularly preferred embodiment, all of the component parts of each unit except for component (iv) are identical to the all of the component parts used in all of the other units of the apparatus. For the avoidance of doubt, the liquids which flow through the apparatus are not component parts of the apparatus. These embodiments are advantageous because the large degree of commonality between the component parts in each unit mean that a smaller inventory of spare parts is required. Still further, routine maintenance of the apparatus is simplified because the units are so similar and the apparatus is easier to operate because each unit is so similar to the other units of the apparatus. In contrast to the prior art which uses very different processing units from multiple manufacturers, engineers avoid the need to learn how to service numerous very different processing units. Component (iv) in each unit typically differs from the component (iv) in other units (so that each unit can perform a discrete processing operation), hence the words "other than component (iv)".

In a preferred embodiment, all of the units of the apparatus are substantially identical except for the device (iv). In this embodiment, the device (iv) may be identical in two or more of the units but more typically the device (iv) is different from one unit to the next, e.g. as illustrated in FIG. 1, so that each unit can perform a discrete processing operation.

In a preferred embodiment the flow path used in at least half of the units (preferably all of the units) have substantially the same configuration.

The flow path is preferably constructed from a plastics material.

Preferably the flow path through each unit is substantially identical to the flow path through all of the other units.

In certain embodiments, one or more of the units (preferably all of the units) comprise a multi-use flow path constructed from materials, e.g. stainless steel, that allow significant number of re-uses before replacement is required.

In certain embodiments one or more of the units (preferably all of the units) comprise a single-use flow path, preferably constructed from materials, e.g. plastics materials, commonly selected to be able to be sterilised by gamma irradiation, that are typically designed with a limited lifetime, for example to be utilised as a disposable consumable.

In one embodiment the product stream from each unit other than the final unit is fed directly to the next unit. In many embodiments, it is often convenient for the product stream of one more of the units to be fed into a storage vessel (e.g. a 'break bag') and then be subsequently used as the feedstock for the next unit (if any). In this way one may test the product stream before it enters the next unit, pause the process and so forth.

The feedstock for the first unit may be also be supplied from a storage vessel or, if desired, it may be supplied directly from a cell culture apparatus, e.g. a bioreactor, preferably after clarification. Examples of suitable storage vessels include tanks and bags.

The inlet (i) for the liquid feedstock typically comprises a tube, preferably fitted with a valve (3) and a non-return valve to avoid contamination of the liquid feedstock with the liquid(s) flowing from the multiple inlet flow-controller (ii).

The mAbs which may be purified by the present process are not particularly limited and include complete monoclonal antibodies and fragments of monoclonal antibodies having biological activity, including multivalent and/or multi-specific forms of any of the foregoing.

Naturally occurring mAbs often comprise four polypeptide chains, e.g. two identical heavy (H) chains and two identical light (L) chains inter-connected by disulfide bonds. Each heavy chain typically comprises a variable region ($V_H$) and a constant region ($C_H$), the $C_H$ region comprising in its native form three domains, $C_H1$, $C_H2$ and $C_H3$. Each light chain typically comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is typically composed of three CDRs and four FRs, arranged from amino-terminus to carboxy-terminus in the following order: FR1, CDR1, FR2, CDR2, FR3, CDR3, FR4.

Monoclonal antibody fragments typically comprise a portion of an intact mAb, said portion having a desired biological activity. mAb fragments generally include at least one antigen binding site. Examples of mAb fragments include:

(i) Fab fragments having $V_L$, $C_L$, $V_H$ and $C_H1$ domains;

(ii) Fab derivatives, such as a Fab' fragment having one or more cysteine residues at the C-terminus of the $C_H1$ domain, that can form bivalent fragments by disulfide bridging between two Fab derivatives;

(iii) Fd fragment having $V_H$ and $C_H1$ domains;

(iv) Fd derivatives, such as Fd derivatives having one or more cysteine residues at the C-terminus of the $C_H1$ domain;

(v) Fv fragments having the $V_L$ and $V_H$ domains of a single arm of an antibody;

(vi) single chain antibody molecules such as single chain Fv (scFv) antibodies in which the $V_L$ and $V_H$ domains are covalently linked;

(vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$);

(viii) domain antibody fragments, such as fragments consisting of a $V_H$ domain, or a $V_L$ domain, and antigen-binding fragments of either $V_H$ or $V_L$ domains, such as isolated CDR regions;

(ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

The impurities which may be removed by the process typically include by-products from the process used to prepare the desired mAb, components of the medium used to prepare the mAB (e.g. nutrients), cells, cellular, host cell proteins, DNA, RNA, other proteins, endotoxins and viruses present in or secreted from a mammalian cell.

The multiple inlet flow-controller (ii) preferably comprises variable flow, preferably intermittent flow, inlet valves which regulate the flow of liquid through the flow-controller. The multiple inlet flow-controller comprises at least 2 inlet valves and in many instances comprise up to 8, such as 3, 4, 5, 6 or 7, inlet valves (iia), although more inlet valves could be included if desired. The inlet valves may each have the same dimensions, or one or more of the inlet valves may have different dimensions to some or all of the other inlet valves. In certain preferred embodiments, the volume measured from each inlet valve to the outlet of the flow-controller (ii) is the same for each inlet, and it is highly preferred that both the volume and the path length measured from each inlet valve to the outlet of the flow-controller (ii) is the same for each inlet.

The multiple inlet flow-controller (ii) employed in the present invention also comprises at least one outlet, and whilst two or more outlets may be present, it is preferred that a single outlet is employed.

The valves in the multiple inlet flow-controller (ii) may regulate the flow between a first, relatively low flow rate wherein the liquid remains able to flow and at least a second, higher flow rate. In preferred embodiments, the valves in the multiple inlet flow-controller (ii) are intermittent flow valves, which prevent flow in a first position, but permit flow in at least a second position. Most preferably, all of the valves are intermittent flow valves. The valves may comprise actuators, for example pneumatic or, more preferably, solenoid actuators.

Preferably the valves in the multiple inlet flow-controller (ii) are controlled, most preferably by a programmable control unit (not shown in the drawings), to regulate the opening and closing of the valves in order to achieve the required relative quantities of the input liquids flowing through the multiple inlet flow-controller (ii). This is preferably achieved through cycling, with a pre-determined time period or cycle rate, through the inlet valves in the flow-controller and regulating the opening or closing of each valve according to the required proportion of the cycle time to generate the desired composition of bioprocessing liquid. The cycle rate can be either constant or varied. Most preferably, intermittent flow inlet valves are employed, and are controlled such that in operation, only one valve is open at any given time. In many embodiments, the cycle rate of the multiple inlet flow-controller (ii) is maintained as a constant and the desired relative quantities of the input liquids used to make the bioprocessing liquid remains consistent.

In many embodiments, the process comprises multiple cycles of flow through the multiple inlet flow-controller (ii). The number of cycles employed will depend on numerous factors such as the duration of the process, the volume of liquid feedstock being processed and the flow rate and the maximum operating pressure of the apparatus. In certain embodiments, at least 10 cycles, such as at least 50, 100, 500, 750, 1000, 1500, 2000, 3000, 5000, 7500, 10000 or more cycles can be employed.

It will be recognised that a range of cycle frequencies can be employed. In many instances, the frequency is less than 100 Hz, typically less than 50 Hz, commonly less than 10 Hz, and preferably less than 5 Hz. In certain preferred embodiments, the frequency is 2 Hz or less, most preferably 1 Hz or less, such as from 0.05 to 0.5 Hz.

In a preferred embodiment the bioprocessing liquid is provided by combining at least three liquid streams ($2ab$), ($2cd$), ($2ef$), at least two (preferably all three) of the at least three liquid streams each being provided by combining at least two further liquid streams (e.g. using valves ($3a$) and ($3b$) or ($3c$) and ($3d$)). This combining is preferably performed in the mixer (iii). The at least three liquid streams ($2ab$), ($2cd$), ($2ef$) may be prepared by combining the liquid streams ($2a$) and ($2b$), ($2c$) and ($2d$) and ($2e$) and ($2f$) respectively.

The composition of the bioprocessing liquid used in a unit may remain the same throughout the process or the composition may change during the process. For example, the composition of the bioprocessing liquid may be changed gradually or stepwise during the process, particularly when the unit comprises a chromatography column and the bioprocessing liquid acts as an eluent.

Liquids (e.g. the at least two other liquids) that can be used to prepare the bioprocessing liquid (e.g. as the further liquid streams as mentioned above) include those known in the art for carrying out the appropriate processing operation. Examples of such liquids include acidic, neutral and basic solutions, for example those having a pH in the range of from 2.5 to 14. Examples include aqueous solutions comprising one or more of the following: sodium potassium or ammonium hydroxide, phosphoric, sulphuric, hydrochloric or acetic acid; salts, e.g. aqueous solutions having a salt concentration of up about 3M, including sodium, calcium, potassium, and ammonium salts, for example phosphate, chloride, acetate, citrate and sulphate salts; buffers, examples of which are well known in the art; reducing agents (e.g. DTT (DL-dithiothreitol) and TCEP ((tris(2-carboxyethyl)phosphine)); amino acids (e.g. histidine, arginine and glycine); detergents (e.g. Tween™ 20 and Triton™-X100); water-miscible organic solvents, e.g. polyols, for example glycerol and polyethylene glycols; and mixtures comprising two or more of the foregoing.

Whilst some mixing may arise from the in-line combination of the flows from the inlet (i) and the flow-controller (ii) outlet, and/or in the means for imparting flow (v), the module further comprises mixer (iii). Mixer (iii) provides a means for combining the liquid feedstock and the liquids (2ab), (2cd), (2ef) and/or the liquid from inlet (2g) used to form the bioprocessing liquid, if desired, to produce a device feed. Furthermore, mixer (iii) may also be used for combining the at least two other liquids (2ab), (2cd), (2ef) and/or (2g) to prepare bioprocessing liquid(s) (e.g. eluents for chromatography) which are subsequently fed to device (iv). Mixer (iii) can be, for example, an in-line mixer or, more preferably, a mixing chamber. Prefer mixer (iii) comprises a static mixer, most preferably a time-delay, split flow static mixer. In many embodiments, the means (iii) is an in-line mixer located downstream of the means for imparting flow (v) (e.g. pump) and upstream of the device (iv) for achieving the processing operation.

In many embodiments, the mixer (iii) further comprises a means for trapping air bubbles, e.g. a bubble trap.

In one embodiment the means (iii) is used for combining the at least two liquids received from the multiple inlet flow-controller (ii), either in the presence or absence of the liquid feedstock. Combining the at least two liquids received from the multiple inlet flow-controller (ii) in the absence of the liquid feedstock is useful for preparing a bioprocessing liquid which is passed through the device (iv) before or after the liquid feedstock has entered component (iv). For example, when the device (iv) comprises a chromatography column, the means (iii) can be used to provide a bioprocessing liquid for conditioning the column before the liquid feedstock has been charged onto the chromatography column, for preparing a bioprocessing liquid for washing the mAb on the chromatography column, for preparing a bioprocessing liquid for eluting the mAb from the chromatography column and for preparing a bioprocessing liquid for removing impurities which remain on the column after the mAb has been successfully eluted from the column in purified form. Preferably at least one of the units (preferably at least half of the units, more preferably all of the units) further comprises a device for removing air bubbles from one or more of the liquids passing through that unit.

The inlet for the device feed may also be used for receiving the bioprocessing liquid(s), e.g. from component (ii) or (iii).

In addition to the devices specified in (III) and (IV) for performing the process operations of chromatography and viral inactivation, the apparatus optionally further comprises one or more units for performing one or more of the following processing operations: chromatography (which may be the same as or different to the chromatography operation performed in device (III)), viral inactivation (which may be the same as of different to the viral inactivation performed in device (IV)), filtration (e.g. ultrafiltration, microfiltration, dead end filtration and/or diafiltration), virus removal, refolding, flocculationand in-line conditioning.

Chromatography bioprocessing operations that can be performed using a device (iv) include affinity chromatography (e.g. Protein A affinity chromatography), ion-exchange (either or both anion and cation exchange) chromatography, hydrophobic interaction chromatography (HIC), reverse-phase chromatography, expanded bed chromatography, mixed-mode chromatography, membrane chromatography and size exclusion chromatography (SEC). In many embodiments, at least one of the units performs the processing operation of Protein A affinity chromatography. Devices for performing chromatography operations comprise the appropriate chromatography apparatus, such as a membrane, fibre monolith or resin. The number and sequence of units performing chromatography will be selected according to the nature of the mAb.

Preferably the apparatus comprises at least two, more preferably three units comprising components (i) to (v) for performing chromatographic purification of the mAb. In this case, the chromatographic purifications performed in each unit preferably use different conditions and/or chromatography columns packed with different materials (e.g. different resins, membranes or monoliths) to the chromatography columns to those used in all of the other units. In a particularly preferred embodiment, at least one of the unit performs affinity chromatography, at least one of the unit performs cation exchange chromatography at least one of the unit performs anion exchange chromatography.

The device(s) (iv) for performing the process of viral inactivation in the process of the present invention commonly comprise a storage vessel in which a liquid comprising the mAb can be stored under conditions which inactivate any viruses which are present. In certain embodiments the outlet and the inlet of the viral inactivation device (iv) can be fluidly connected to generate a re-circulation loop. In one such embodiment the apparatus is set up with a vessel or bag fluidly connected between the "device" inlet and "device" outlet and one of the apparatus outlets is fluidly connected to one of the multiple inlet flow-controller (ii) inlets. The vessel or bag between the device (iv) "inlet" and "outlet" being fluidly connected to the liquid feedstock inlet (i) is filled by the means to impart flow (v), typically a pump, or conditioned with at least one other liquid through at least one of the other multiple inlet flow-controller (ii) inlets. In certain embodiments the vessel or bag is a mixing vessel or bag. The bioprocessing liquid is re-circulated through the inlet of the multiple inlet flow-controller (ii) to the vessel or bag and back to the inlet of the multiple inlet flow-controller (ii) as the solution comprising the mAb is conditioned by at least one additional liquid fluidly connected to at least one other inlet on the multiple inlet flow-controller (ii).

The viral inactivation may be performed by a number of techniques using conditions known in the art. For example, using a chromatography column, a chromatography membrane, or a holding tank that is capable of incubating a fluid comprising the liquid feedstock at a pH of less than about 4.0, e.g. a pH between about 3.0 to about 4.0, preferably a pH between about 3.2 to about 3.9, especially a pH between about 3.4 to about 3.8 and more especially a pH between about 3.45 to about 3.7. Preferably the liquid feedstock is held at the aforementioned pH for a period of at least 25 minutes, e.g. for a period of between about 30 minutes to 1.5 hours, preferably a period of between about 30 minutes to 1.25 hours, more preferably a period of between about 0.75 hours to 1.25 hours and especially a period of about 1 hour. In each case the conditions chosen are such that the mAb is not damaged or destroyed.

Inactivated viruses can be removed by filtration, for example using a normal flow filter (NFF) or a tangential flow filtration (TFF) filter such as is described in U.S. Pat. No. 6,365,395. In either TFF mode or NFF mode, filtration to remove inactivated viruses is conducted under conditions to retain the inactivated virus, generally using membranes having an average pore diameter of 20 to 100 nanometer (nm). Such membranes retain inactivated viruses on the membrane surface while permitting passage of the mAb through the membrane.

The unit(s) for removing inactivated viruses may also remove any viruses which survive the virus inactivation step.

Representative suitable ultrafiltration membranes that can be used to remove inactivated viruses (along with any viruses that remain active include membranes formed from regenerated cellulose, polyethersulfone, polyarylsulphones, polysulfone, polyimide, polyamide, polyvinylidenedifluoride (PVDF) or the like and are known as VIRESOLVE® membranes and RETROPORE™ membranes available from EMD Millipore, Billerica, Mass. These can be supplied in either a cartridge (NFF) form, such as VIRESOLVE™ NFP viral filters, or as cassettes (for TFF), such as PELLICON™ cassettes, available from EMD Millipore, Billerica, Mass.

Filtration operations that can be performed using a device (iv) include viral, depth and absolute filtration, ultrafiltration, diafiltration and microfiltration. In many embodiments, the filtration device (iv) comprises a filter module between the device inlet and device outlet. The filter module may be flushed and chased using at least two liquid feeds attached to the multiple inlet flow-controller inlets (ii) and the feedstock comprising the target mAb may be fluidly connected to the feedstock inlet (i). Processing of the liquid feedstock through a filtration device (iv) is achieved through the means (v) for imparting flow fluidly connected to and positioned downstream of the multiple inlet flow-controller outlet (ii) and feedstock inlet (i), and upstream of the filtration device (iv). The filters are often in modular form and may employ configurations which are known in the art of purifying biomolecules.

Ultrafiltration and/or diafiltration may be employed to concentrate or to perform buffer exchange.

Viral filtration, depth filtration and absolute filtration process operations are known in the art and can be performed using commercially available filtration devices. In many embodiments the filtration device or devices are placed between the device (iv) inlet and outlet, in order to perform filtration as the processing operation. In another embodiments an additional filter device is positioned downstream of the apparatus outlet, which in certain embodiments allows the apparatus to perform most of the purification steps, such as chromatography, viral inactivation, tangential flow filtration, viral filtration or depth filtration, followed by a secondary filtration operation external to the apparatus.

Tangential flow filtration ("TFF") processing operations that can be performed using the apparatus of the present invention include conventional recirculating TFF and single pass TFF ("SPTFF"). In certain embodiments the outlet and the inlet of the apparatus can be fluidly connected to generate a re-circulation loop, an example being re-circulating tangential flow filtration.

In one embodiment, the apparatus comprises a unit comprising a TFF device (iv), for example a TFF device comprising a flat sheet, hollow fibre or spiral wound membrane between the device (iv) inlet and device (iv) outlet and the retentate from the unit comprising a TFF device (iv) may be directed from one of the apparatus outlets to a fluidly connected inlet on a vessel or bag, containing at least one inlet and one outlet. The outlet of the vessel or bag may be fluidly connected to the liquid feedstock inlet (i). The vessel or bag may be maintained at a constant level using an auxiliary means to supply the feedstock or liquid into the vessel or bag by being fluidly connected to a second inlet on the vessel or bag. In another embodiment, the apparatus is set up with a unit comprising a TFF device (iv) comprising either flat sheet, hollow fibre or spiral wound membranes between the device inlet and device outlet and the retentate from the unit comprising a TFF device (iv) is fluidly connected from one of the apparatus outlets back to one of the inlets of the multiple inlet flow-controller valve (ii). In certain embodiments the re-circulation loop from the apparatus outlet to its inlet (i) contains a break vessel or bag. A solution comprising a target mAb or a liquid is drawn into the re-circulation loop through the liquid feedstock inlet by a means for imparting flow, typically a pump. The retentate is re-circulated through the unit comprising a TFF device (iv), preferably through one of the multiple inlet flow-controller inlets. The multiple inlet flow-controller (ii) may be employed to mix the retentate with at least one other liquid. Operation of recirculating TFF is known in the art and may be controlled through setting a cross-flow rate and trans-membrane pressure.

In certain embodiments the apparatus comprises a unit comprising a SPTFF device (iv). The SPTFF device preferably comprises either flat sheet, hollow fibre or spiral wound membranes between the device (iv) inlet and device (iv) outlet, for example as described in WO2017/118835. In some embodiments a hybrid of SPTFF and (re-circulating) TFF can be employed, where the retentate generated using a variable flow valve downstream of the device (iv) is returned to the feed inlet (i).

The device (iv) preferably optionally comprises an outlet for the waste stream. However this is not essential in many embodiments because the waste stream, when present, may exit the device using the same outlet as the product stream. For example, when the device (iv) comprises a chromatography column only one stream exits the column and this stream typically begins as a waste stream containing impurities until the desired mAb is eluted from the column. Then, for a period of time, the stream exiting the column comprises the mAb minus many impurities. Finally, the amount of mAb exiting the column reduces and the liquid exiting the device typically contains largely impurities.

The processing units and apparatus used in the present process preferably comprises a bubble trap, pressure sensor, temperature sensor, pH sensor, flow rate sensor, conductivity sensor, air sensor and/or uv sensor, e.g. a uv/visible multi-wavelength sensor. One or more of each of the foregoing may be present.

Means (v) for imparting flow of liquids are well known in the art and include the application of gas pressure to a liquid, especially an inert gas, such as nitrogen or helium. Preferably the means (v) for imparting flow of the liquids comprises one or more pumps. Pumps which can be employed include peristaltic, diaphragm, lobe and centrifugal pumps. Both disposable and re-usable pumps can be employed. In many preferred embodiments, each unit comprises a single pump (v) (i.e. the unit has one and only one pump), preferably located downstream of component (ii) and upstream of component (iv). The type and size of the pump (v) selected is commonly dependent on the flow capacity and pressure profile appropriate to the scale and design parameters of the apparatus. In certain highly preferred embodiments, the pump (v) is a quaternary diaphragm pump.

In one particular embodiment of the present invention, one or more of the units (preferably all of the units) comprise one or more of the following:

(vii) a device for preparing each of the at least two liquids used to form the bioprocessing liquid;

(viii) a device for trapping air bubbles from one or more of the liquids passing through the unit;

(ix) a means downstream of the device (iv) outlet to regulate pressure;

(x) a number of sensors (27) appropriate for monitoring the processing operation, said sensors (27) being located upstream and/or downstream of the device (iv) inlet and device (iv) outlet; and (xi) at least one outlet in fluid connection with the feed inlets.

Preferably one or more of the units (preferably all of the units) further comprise a means for applying additional pressure to liquids flowing through the device (iv) located downstream of the device (iv). Means for imposing pressure are known in the art and include pinch valves, diaphragm valves, especially variable position diaphragm valves.

In many embodiments, the process is operated under the control of a programmable control unit, preferably a computer. In some embodiments, a single control unit controls two or more units operations. In other embodiments, each unit is under the control of a separate control unit. In these other embodiments, preferably the units employ a common programming language, which enables simplified communication between the units.

In one embodiment at least one (preferably half, more preferably all) of the units of the apparatus further comprise at least one switchable bypass assembly (vi) which direct the flow of the liquid feedstock and/or liquids which are to be combined to form the bioprocessing liquid to either (a) the mixer (iii) for combining the liquid feedstock and liquids (2ab), (2cd), (2ef) and/or (2g) to produce a device feed or (b) bypass the means (iii) and instead send the liquids and/or feedstock to the device (iv) without passing through the means (iii). The units of this embodiment have the advantage that they may be used for the purification of fragile mAbs where combining the liquid feedstock and the bioprocessing liquid in the mixer (iii) could or would damage or degrade the mAb.

The switchable bypass (vi) is particularly useful when the device (iv) comprises a chromatography column. The switchable bypass (vi) can be used to charge a mAb onto the chromatography column (iv) without passing through mixer (iii) and then mixer (iii) can be used to prepare a bioprocessing liquid which acts as eluent for the mAb already present on the column (iv). Furthermore, it can sometimes be useful to bypass the mixing means (iii) when the device (iv) performs the process steps of ultrafiltration and/or diafiltration where hold-up volumes and product stability could otherwise be a problem.

The switchable bypass assembly (vi) preferably comprises tubing and two or three valves which direct the flow of the liquid feedstock and liquids (2ab), (2cd), (2ef) and/or (2g) either to the mixer (iii) or to the device (iv) without passing through the mixer (iii).

One embodiment of apparatus according to the present invention is described with reference to FIG. 2. A first processing unit comprises an inlet (i) for the liquid feedstock and inlets (2a) to (2f) for six different buffers plus an inlet (2g) for water for injection are provided. Each inlet is fitted with a valve, such as straight-through diaphragm valve, (3) and (3a) to (3g), to enable the flow to be switched on or off. In the embodiment shown, buffer feeds from inlets (2a) and (2b), (2c) and (2d) and (2e) and (2f) are combined downstream of the valves, (3a) and (3b), (3c) and (3d), and (3e) and (3f) respectively, to form three buffer feed lines (2ab), (2cd) and (2ef) respectively, which are fluidly connected, along with the water for injection inlet (2g) to different inlets on a multiple inlet flow controller, (ii), comprising a four valve manifold with a single outlet having a fast acting pneumatic actuator. By this configuration, and by appropriate opening and closing of valves (3a) and (3b), (3c) and (3d), and (3e) and (3f), allows selection between buffers from inlets (2a) and (2b), (2c) and (2d) or (2e) and (2f), thereby increasing the flexibility of operation of the unit. The outlet from the multiple inlet flow controller, (ii), is in fluid connection with the feed for a liquid comprising a target mAb at position (5), upstream of a pump, (v), which imparts flow of the combined feeds through a static mixer (iii) fitted with a bubble trap, (8), and to the inlet of first chromatography column, (iv). The line feeding the output from the pump, (v), to the chromatography column, (iv), is fitted with a pressure sensor, (7), air sensor, (9), a flow meter, (10), such as an ultrasonic flow meter and a combined temperature and conductivity sensor, (11). In some embodiments, the pump, (v), is controlled via a programmable control unit in response to a feedback signal, (29), from the flow meter, (10).

In some embodiments, optionally, the multiple-inlet flow controller, (ii), is controlled via a programmable control unit in response to a feedback signal, (28), from the conductivity and temperature sensor, (11). The outlet line from the chromatography column, (iv), is provided with pressure sensor, (13), a combined temperature and conductivity sensor, (14), a uv detector, such as a uv/visible multi-wavelength detector, (15), a pH sensor, (16), and a variable position valve, (30), which can be employed to regulate pressure and to impose back pressure if desired. Preferably, the operation of the pump, (v), and the variable position valve, (30), and thereby the regulation of the pressure in the apparatus, are controlled via a programmable control unit in response to feedback signals, (26) and (27), from the pressure sensors, (7) and (13). The outlet line passes through a series of valves, (17), (19) and (20), which enable the flow to be controlled between an outlet (18) for the product stream containing purified monoclonal antibody, an outlet (21) for the waste stream comprising at least some of the impurities, or an the outlet, (22), for example enabling collection or sampling. The apparatus is further fitted with valves, (23a) and (23b), which enable the flow to be diverted to bypass the column, (iv), if required during operation, and further valves, (24) and (25), which enable flow through the column (iv) to be halted. The product stream passing through outlet (18) can then be employed as the feedstock comprising a target mAb in a second unit for performing a second processing operation, configured as illustrated in FIG. 2, but where preferably the chromatography column, (iv), is replaced with a different means for performing a processing operation, such as a different type of chromatography, or a non-chromatographic unit operation, and wherein in the second unit for performing a second processing operation, the feedstock fed into inlet (i) comprises the product stream exiting the previous unit from outlet (18).

In one method of operation, valve (3) is opened, whilst valves (3a) to (3g) are closed, and the liquid feedstock comprising a monoclonal antibody and impurities is fed by the pump, (v), to the column, (iv), to load the column with the monoclonal antibody and impurities, for example a column comprising Protein A affinity resin, such that the monoclonal antibody selectively binds to the Protein A affinity resin. On completion of the desired loading, valve (3) is closed, and one or more of valves (3a) to (3g) is opened, to enable one or more of the liquids from inlets (2a) to (2g) which form the bioprocessing liquid to be pumped through the column, (iv). In some embodiments, initially only valve (3a) is opened, and multiple-inlet valve (ii) is operated so as to open the inlet valve to which buffer from inlet (2a), which may be a wash buffer, is supplied, such that the loaded column (iv) is washed with the buffer from inlet (2a). On completion of the desired washing stage, one or more of valves (3b) to (3g) may be opened, with valve (3a) either remaining open or being closed. The inlet valves on the multiple inlet flow-controller, (ii) are opened in order to allow the liquids from inlets (2b) to (2g), or mixtures comprising two or more thereof, to be pumped through the column, (iv). By controlling the opening and closing of the valves on the multiple inlet valve, (ii), and/or the valves (3a) to (3g), the composition of the bioprocessing liquid fed to the column (iv) can be altered and controlled as desired. For example, where valves (3b), (3c) and (3e) are open, changing the inlet valve which is open in the multiple-inlet flow controller, (ii), and closing the others, enables the composition of the bioprocessing liquid to be changed in a stepwise or gradual manner. In another example, two or more of the inlet valves of the multiple-inlet flow controller, (ii) can be opened and closed at a given frequency, and for a chosen period of time to enable a given mixture of the liquids to be fed to the column, (iv). Adjustment of the times and/or frequency that the inlet valves on the multiple inlet valve, (ii), are open or closed, allows the composition of the bioprocessing liquid to be altered. Where the times and/or frequency are altered in stepwise fashion, the composition of the bioprocessing liquid also changes in a stepwise manner. Where the times and/or frequency are altered gradually over a period of time, the composition bioprocessing liquid also changes gradually, enabling the application of a gradient to the column, (iv). By whichever desired method, the liquid composition of the bioprocessing liquid fed to the column (iv) may be changed to a composition which causes the mAb to elute from the column (iv). Prior to elution, liquids exiting from the column (which may comprise impurities), (iv) are either collected via the outlet, (22), or sent to waste, (21), and valves (17), (19) and (20) are set accordingly. When the product stream containing purified monoclonal antibody mAb reaches valve (17), valves (19) and (20) are closed, and valve (17), opened, allowing the purified mAb to pass through the outlet (18) to the second unit and enter the second unit through its inlet (i) as the liquid feedstock for the second unit.

Operation of the second unit and any further units can be substantially as described above in relation to the first unit. It will be recognised that the mAb exiting the second unit through its outlet (18) may either be recovered and used as is, or may be further purified by acting as the feedstock for a further processing operation. Such further processing operation may employ conventional apparatus, or further units according to the configuration illustrated in FIG. 2, or otherwise according to the present invention.

The process according to the present invention further comprises the step of mixing the resultant, purified monoclonal antibody with one or more pharmaceutically acceptable carriers to form a medicament.

The entire subject matter of the claims is hereby incorporated into this description by reference thereto.

The present application is illustrated without limitation by the following example.

EXAMPLE

Figure 2:
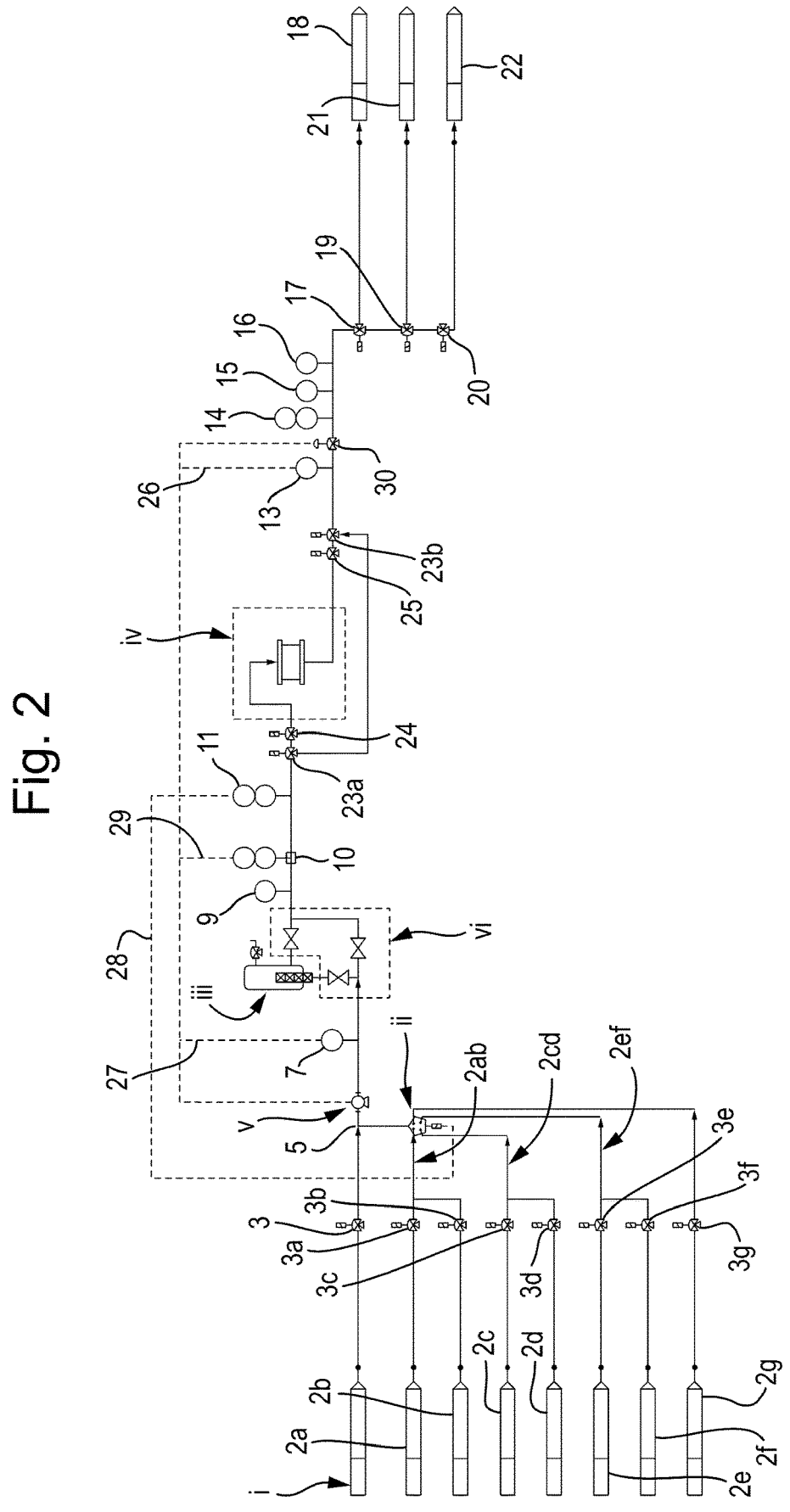
FIG. 2 is a schematic view of one processing unit which may be used to perform a processing operation.

An apparatus may be constructed comprising two units in series, wherein each unit has the general construction shown in FIG. 2 and each unit comprised the flow path illustrated in FIG. 3. The device (iv) in the first unit comprises a chromatography column and the device (iv) in the second unit comprises a means for performing viral inactivation.

Construction of the First and Second Processing Units

Each processing unit may be constructed comprising the components shown in FIG. 2 except that valve (23b) is replaced with a simple fluid connection. Each unit comprises a substantially identical flow path.

Preparation of the Bioprocessing Liquids

Stock solutions SS1 to SS7 described below may be used as the streams for inlets (2a) to (2g) as indicated:
inlet (2a)—1M sodium chloride (SS1);
inlet (2b)—4M sodium chloride (SS2);
inlet (2c)—250 mM dibasic sodium phosphate (SS3);
inlet (2d)—100 mM sodium acetate (SS4);
inlet (2e)—175 mM monobasic sodium phosphate (SS5);
inlet (2f)—1M acetic acid (SS6); and
inlet (2g)—distilled water (SS7).

The seven stock solutions SS1 to SS7 may be combined in the proportions shown in Table 1 using a multiple inlet flow-controller (ii) to give the five bioprocessing liquids BPL1 to BPL5 indicated in Table 1:

TABLE 1

| Bioprocessing Liquids | | | | | | |
|---|---|---|---|---|---|---|
| | | | Stock solution | | | |
| Bioprocessing liquid | SS1 1M NaCl (%) | SS2 4M NaCl (%) | SS3 250M Na$_2$HPO$_4$ (%) | SS4 100 mM NaCH$_3$O$_2$ (%) | SS5 175 mM NaH$_2$PO$_4$ (%) | SS6 1M C$_2$H$_4$O$_2$ (%) | SS7 Water (%) |
| BPL1 (equilibration) | 15 | — | 7 | — | 2 | — | 76 |
| BPL2 (wash 1) | — | 13 | 7 | — | 1 | — | 79 |
| BPL3 (wash 2) | — | — | 2 | — | 26 | — | 72 |
| BLP4 (elution) | — | — | — | 3 | — | 5 | 92 |
| BPL5 (strip) | — | — | — | — | — | 10 | 90 |

First Processing Unit-Chromatography

The processing unit comprises a chromatography column as device (iv) (2.5 L mAbSelect SuRe resin column). The chromatography column (iv) is loaded through inlet (i) with an feedstock comprising a mAb and impurities and chased with 2 L of a pre-made solution of BPL1.

The bioprocessing liquids BPL1 to BPL5 may be generated through proportionally selecting each of the stock solutions SS1 to SS7 using the multiple inlet flow-controller, (ii), and the downstream pump, (v), and the static mixer, (iii). During the establishment of the correct buffer composition as bioprocessing liquid, the column, (iv), is by-passed through valve (23a), with valves (24) and (25) closed, the unwanted buffer being directed to the waste, (21). Once the buffer is homogeneous, as indicated by a steady reading from the upstream conductivity sensor, (11), the buffer is supplied as the bioprocessing liquid to the chromatography column, (iv), by opening valves (24) and (25) and closing the by-pass line at valve (23a). The process conditions may be monitored using the conductivity, UV and pH sensors, (14), (15) and (16), downstream of the column, (iv). During the conditioning of the column (iv) ahead of the binding of the mAb to the column and post-use water rinse the liquid is directed to waste, (21). Once conditioned with BPL1, the chromatography resin is loaded with the liquid feedstock comprising the monoclonal antibody and impurities drawn-in through the feedstock inlet, (i), by the action of the pump, (v), bypassing the static mixer, (iii), using the switchable bypass assembly, (vi), and onto the column, (iv). The flowthrough from the column (iv) is collected through the exit outlet, (21), whilst the first buffer wash BPL2 is collected through the outlet (22), and the second buffer wash BPL3 is collected through the exit outlet (21). The purified mAb is recovered from the column (iv) using the elution buffer BPL4 as bioprocessing liquid and collected through the outlet (18). Finally, the remaining impurities may then be removed from the column (iv) using the strip buffer BPL5 as bioprocessing liquid and collected through the outlet (22).

Second Processing Unit—Viral Inactivation

The processing unit comprises a viral inactivation device (iv) (50 L Stedim Magmix™ bag with impeller drive) with outlet (21) connected to inlet (2g) to provide a re-circulation loop.

Preparation of the Bioprocessing Liquids

Stock solutions SS1 to SS2 described below were attached to the inlets (2a) to (2g)-in the following order:
inlet (2a)—1M acetic acid (SS1);
inlet (2b)—no feed;
inlet (2c)—1M Tris base (SS2);
inlet (2d)—no feed;
inlet (2e)—no feed;
inlet (2f)—no feed; and
inlet (2g)—device bag (iv).

The product stream from the first processing unit is used as feedstock for the second processing unit by loading it into the viral inactivation bag (iv) of the second processing unit through inlet (i). Thus feedstock comprises a mAb and viruses (25 L~7.5 g/L mAb in 50 mM sodium acetate pH 4.6). The feedstock bypasses the device (iii) using the switchable bypass assembly (vi) through the pump (v) and directed to the device (iv) through opening valve (24) and closing the by-pass line at valve (23a) and valve (25). Once the device (iv) is charged, valve (25), (19), (3g) and the multi-flow controller valve connected to (3g) may be opened. Valve (3) is closed and the switchable bypass assembly (vi) is left in bypass mode. The impeller drive in the viral inactivation bag is turned on and set to a speed of 450 rpm. The pH of the feedstock is reduced to a target of pH 3.6 by the intermittent addition of 1M acetic acid at (2a) connected to the multiple-inlet flow controller (ii) through (2ab). Valve (3a) is opened for the duration of the pH titration down to pH 3.6 and the multiple-inlet flow controller (ii) is operated to dose approximately 100 mL of 1M acetic acid into the viral inactivation bag (iv) every 30 seconds, each time through the action of the valves. After eight doses of 1M acetic acid the feedstock is re-circulated around the flow path and mixed in the viral inactivation bag (iv) for 15 min. Acetic acid dosing is repeated as described above until the pH during the 15 min re-circulation reaches pH 3.6, as determined by sensor (15). The pH titrated feedstock is then re-circulated around the flow path and mixed in the viral inactivation bag (iv) for 60 min.

The pH of the feedstock is increased to a target of pH 5.0 by the intermittent addition of 1M Tris base at (2c) connected to the multiple-inlet flow controller (ii) through (2cd). Valve (3c) is opened for the duration of the pH titration up to pH 5.0 and the multiple-inlet flow controller (ii) is operated to dose approximately 100 mL of 1M Tris base into the viral inactivation bag (iv) every 30 seconds, each time through the action of the valves. After eight doses of 1M Tris base the feedstock is re-circulated around the flow path and mixed in the bag (iv) for 15 min. Tris base dosing is repeated as described until the pH during the 15 min re-circulation reaches pH 5.0, as determined by sensor (15). Finally, the product stream comprising the mAb and inactivated viruses is recovered by closing outlet (19) and opening valve (17) to collect the contents of the viral inactivation bag (iv) as product stream through outlet feed (18).

The invention claimed is:
1. A process for purifying a liquid feedstock comprising a monoclonal antibody and impurities, the process comprising passing the liquid feedstock through an apparatus comprising at least two processing units, each such unit producing a product stream containing purified monoclonal antibody and optionally a waste stream comprising at least some of the impurities, wherein each unit comprises the following components (i) to (v):
   (i) an inlet for the liquid feedstock;
   (ii) a multiple inlet flow-controller comprising two or more variable flow inlet valves for producing a bioprocessing liquid from at least two other liquids to be combined in a desired ratio;
   (iii) a means for combining the liquid feedstock and the bioprocessing liquid to produce a device feed and/or for combining the at least two other liquids to prepare the bioprocessing liquid;
   (iv) a device for performing a processing operation on the liquid feedstock or on the device feed, the device comprising an inlet for the device feed and/or the liquid feedstock and an outlet for a product stream; and
   (v) a means for imparting flow of the liquid feedstock, the at least two liquids, the bioprocessing liquid, the device feed, the product stream and the optional waste stream;
   wherein:
   the units are arranged in series such that the liquid feedstock for the second and any subsequent units comprises the product stream from the preceding unit;

the device (iv) in at least one of the at least two processing units performs the processing operation of chromatography; and the device (iv) in at least one of the at least two processing units performs the processing operation of viral inactivation, wherein the bioprocessing liquid is produced in the multiple inlet flow controller (ii) by combining the at least two other liquids, and then the liquid feedstock is fed through inlet (i) and is combined with bioprocessing liquid in the means (iii) and then fed through the device (iv) or is combined with the bioprocessing liquid in the device (iv), in either case to give the product stream, and optionally a waste stream which exits the unit.

2. The process according to claim 1 wherein the processing operation of viral inactivation is performed after the processing operation of chromatography.

3. The process according to claim 1 wherein the apparatus comprises a further unit comprising components (i) to (v) for performing an additional chromatographic purification of the mAb.

4. The process according to claim 3 wherein the chromatographic purifications performed in each unit use different conditions and/or chromatography columns packed with different resins to the chromatography columns to those used in all of the other units.

5. The process according to claim 1 wherein each chromatographic purification independently is selected from affinity chromatography, cation exchange chromatography, anion exchange chromatography, mixed-mode chromatography, hydrophobic interaction chromatography, reverse-phase chromatography, expanded bed chromatography, mixed-mode chromatography, membrane chromatography and size exclusion chromatography.

6. The process according to claim 1 wherein each unit prepares its mixed bioprocessing liquid in situ during the process.

7. The process according to claim 1 wherein the apparatus further comprises a unit comprising components (i) to (v) for removing any viruses from its liquid feedstock.

8. The process according to claim 1 wherein the apparatus further comprises a unit comprising components (i) to (v) for ultrafiltration of its feedstock in order to provide a concentrate comprising the target material.

9. The process according to claim 1 wherein the apparatus further comprises a unit comprising components (i) to (v) for diafiltration of its feedstock in order to buffer the target material at a pH at which the target material is stable.

10. The process according to claim 1 wherein the means for imparting flow in each unit comprises a single pump.

11. The process according to claim 1 wherein the apparatus comprises the following units arranged in series, each unit comprising the components (i) to (v) and with the product feed of each unit being used as the feedstock for the next unit or, if there is no next unit, the product feed being collected:

a. a unit for performing chromatographic purification of the mAb by affinity chromatography;

b. a unit for inactivation of any viruses which may be present in the liquid feedstock; and c. a unit for performing chromatographic purification of the mAb by ion exchange chromatography.

12. The process according to claim 1 wherein the apparatus comprises the following units arranged in series, each unit comprising the components (i) to (v) and with the product feed of each unit being used as the feedstock for the next unit or, if there is no next unit, the product feed being collected:

a. a unit for performing chromatographic purification of the mAb by affinity chromatography by affinity chromatography;

b. a unit for inactivation of any viruses which may be present in the liquid feedstock;

c. a unit for performing chromatographic purification of the mAb by cation exchange chromatography; and d. a unit for performing chromatographic purification of the mAb by anion exchange chromatography.

13. The process according to claim 1 wherein the apparatus comprises the following units arranged in series, each unit comprising the components (i) to (v) and with the product feed of each unit being used as the feedstock for the next unit or, if there is no next unit, the product feed being collected:

a. a unit for performing chromatographic purification of the mAb by affinity chromatography;

b. a unit for inactivation of any viruses which may be present in the liquid feedstock;

c. a unit for performing chromatographic purification of the mAb by cation exchange chromatography;

d. a unit for performing chromatographic purification of the mAb by anion exchange chromatography; and e. a unit for removal of any inactivated viruses.

14. The process according to claim 1 wherein the apparatus comprises the following units arranged in series, each unit comprising the components (i) to (v) and with the product feed of each unit being used as the feedstock for the next unit or, if there is no next unit, the product feed being collected:

a. a unit for performing chromatographic purification of the mAb by affinity chromatography;

b. a unit for inactivation of any viruses which may be present in the liquid feedstock;

c. a unit for performing chromatographic purification of the mAb by cation exchange chromatography;

d. a unit for performing chromatographic purification of the mAb by anion exchange chromatography; and a. a unit for concentrating and/or performing buffer exchange of the product stream from the preceding unit.

15. The process according to claim 11 wherein the units are arranged in series in the order listed.

16. The process according to claim 1 wherein the bioprocessing liquid is provided by combining at least three liquid streams, at least two of the at least three liquid streams each being provided by combining at least two further liquid streams.

17. The process according to claim 1 wherein at least one of the units further comprises a device for removing air bubbles from one or more of the liquids passing through that unit.

18. The process according to claim 1 wherein at least one of the units further comprises a pressure sensor located upstream of component (iv).

19. The process according to claim 1 wherein at least one of the units further comprises a pressure sensor located downstream of component (iv).

20. The process according to claim 1 wherein at least one of the units further comprises a UV sensor located downstream of component (iv).

21. The process according to claim 1 wherein at least one of the units further comprises a pH sensor located downstream of component (iv).

22. The process according to claim 1 wherein at least one of the units further comprises a conductivity sensor located downstream of component (iv).

23. The process according to claim 1 wherein at least one of the units further comprises at least one switchable bypass assembly (vi) which directs the flow of the liquid feedstock and bioprocessing liquid to either (a) the means (iii) for combining the liquid feedstock and the bioprocessing liquid to produce a device feed or to (b) bypass the means (iii) and instead send the liquid feedstock and bioprocessing liquid to the device (iv) without passing through the means (iii).

24. The process according to claim 23 wherein the switchable bypass assembly (vi) is present in all of the units.

25. The process according to claim 1 wherein the flow paths used in at least half of the units have substantially the same configuration.

26. The process according to claim 1 wherein at least 75% of the component parts of each unit other than component (iv) are identical to the component parts used in at least 80% of the other units of the apparatus.

27. The process according to claim 1 wherein all of the component parts of each unit except for component (iv) are identical to the all of the component parts used in all of the other units of the apparatus.

28. The process according to claim 1 wherein the composition of the bioprocessing liquid used in at least one of the units is changed stepwise or gradually during the process.

29. The process according to claim 1, wherein each unit comprises one and only one pump.

* * * * *